United States Patent [19]

Svensson

[11] 4,134,300
[45] Jan. 16, 1979

[54] APPARATUS FOR EVACUATING AND THEN COLLECTING MEDIUM SAMPLES IN CONTAINERS SEALED BY A RESILIENT STOPPER AT SUBSTANTIALLY ATMOSPHERIC PRESSURE

[76] Inventor: Jan A. Svensson, Hakarpsvagen 53, S-561 00 Huskvarna, Sweden

[21] Appl. No.: 791,131

[22] Filed: Apr. 25, 1977

Related U.S. Application Data

[60] Division of Ser. No. 717,814, Aug. 26, 1976, which is a continuation-in-part of Ser. No. 608,809, Aug. 28, 1975, abandoned.

[51] Int. Cl.² ............................................. G01N 1/14
[52] U.S. Cl. .................................... 73/425.6; 128/2 F
[58] Field of Search ................ 73/425.6; 128/DIG. 5, 128/2 F, 220

[56] References Cited

U.S. PATENT DOCUMENTS 3,433,216   3/1969   Mattson ..................... 128/DIG. 5

Primary Examiner—Donald O. Woodiel

[57] ABSTRACT

A method and apparatus are provided for reducing the pressure in and then collecting medium samples in containers such as test tubes sealed by a resilient stopper at substantially atmospheric pressure, comprising piercing the stopper at or shortly before the time of collection of a medium sample by a first cannula, connected at one end to a pressure-reducing device, thereby connecting the interior of the container with the pressure-reducing device via the first cannula; evacuating the container to a desired subatmospheric pressure; withdrawing the first cannula; penetrating the stopper by a second cannula connected at one end to a medium source to be sampled, thereby connecting the source with the interior of the container via the second cannula; and then sucking a sample of medium into the container under the influence of the subatmospheric pressure effected in the interior of the container by the pressure reduction.

6 Claims, 14 Drawing Figures

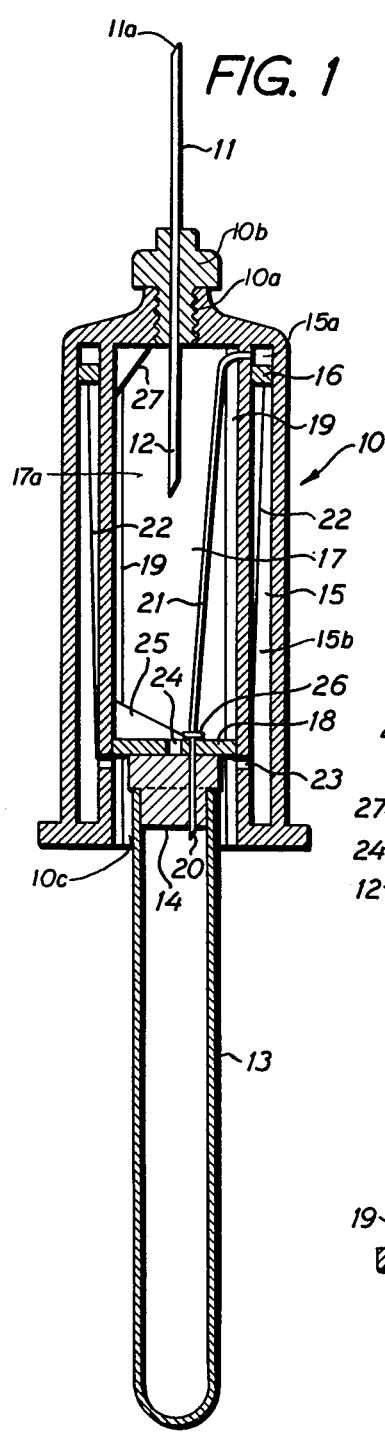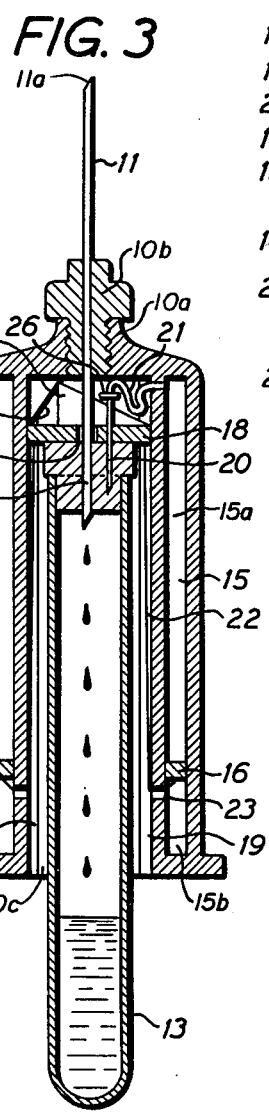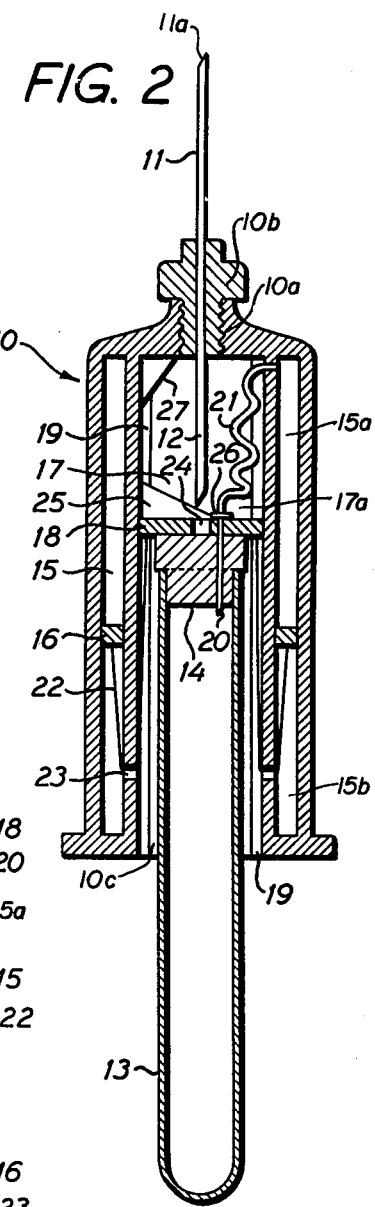

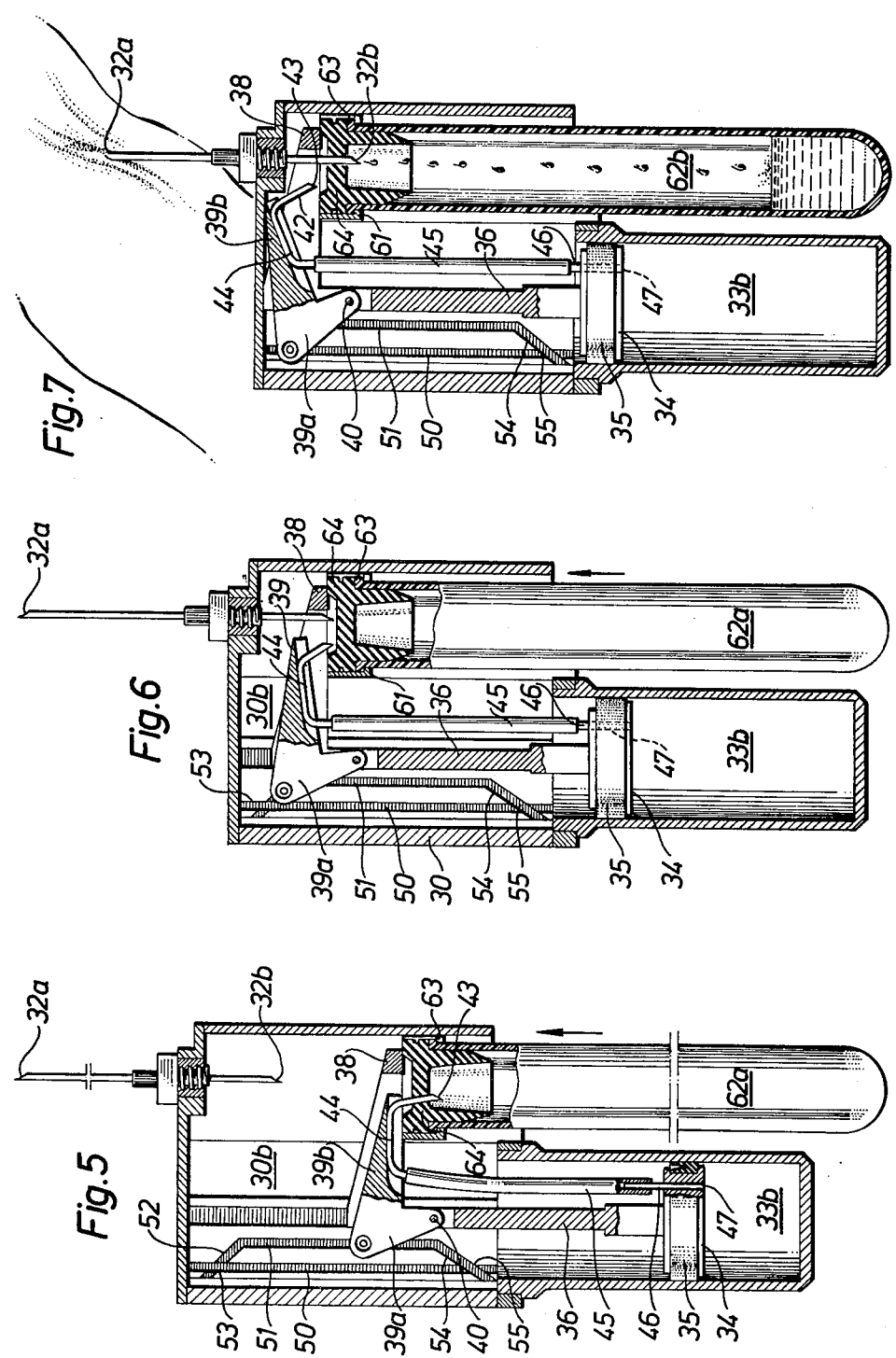

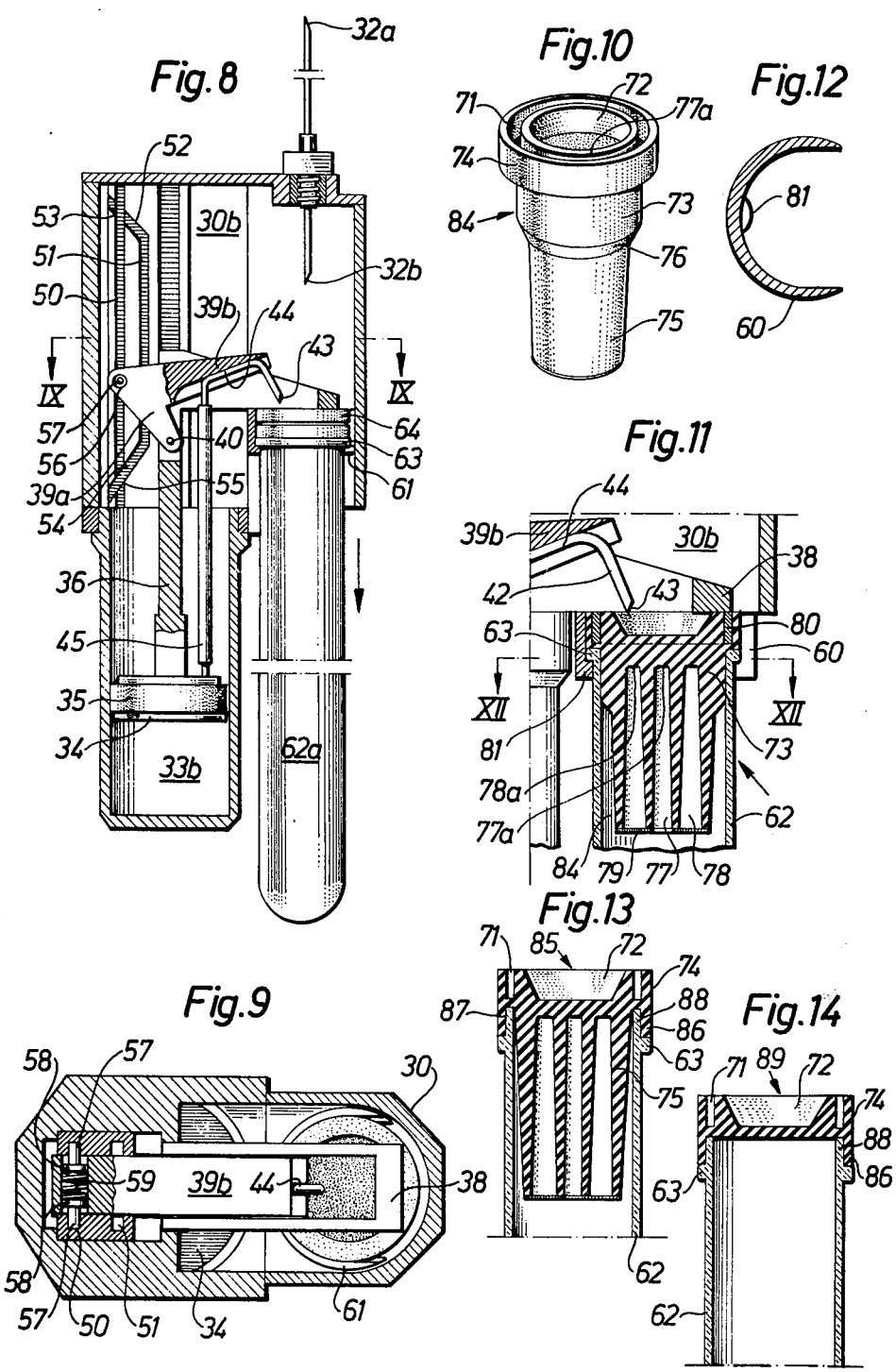

APPARATUS FOR EVACUATING AND THEN COLLECTING MEDIUM SAMPLES IN CONTAINERS SEALED BY A RESILIENT STOPPER AT SUBSTANTIALLY ATMOSPHERIC PRESSURE

This is a division, of application Ser. No. 717,814 filed Aug. 26, 1976, which in turn is a continuation-in-part of Ser. No. 608,809 filed Aug. 28, 1975, now abandoned.

When a large number of blood samples is needed from one patient in hematological examinations, pre-evacuated sample containers, such as test tubes, are normally used. The test tubes are connected to a cannula, which is inserted in a blood vessel of the patient, and the blood flows through the cannula under the higher pressure outside the evacuated test tube. Such devices for taking blood samples are marketed under the trademark VACUTAINER and VENOJECT, and offer considerable advantages in comparison with the conventional method:

(1) since the system is closed, the risk of transmission of infection from blood samples to the blood-taking staff is eliminated;
(2) the method is practical and time-saving;
(3) it is easier and quicker to take samples from elderly patients with bad or fairly bad blood circulation;
(4) the method is easier on the patient, since a single cannula can be used;
(5) the test tubes can be delivered pre-dosed with reagent material for alternative analyses.

Svensson U.S. Pat. No. 3,776,218 granted Dec. 4, 1973, points out that the process of exhausting the test tubes and closing them at a subatmospheric pressure increases substantially the manufacturing cost of the test tubes. As the vacuum tubes must retain a subatmospheric pressure for quite a long time, it is necessary that the test tubes, as well as the stopper, be of diffusion-tight material. Glass is the best material for the test tubes, and butyl rubber the best material for the stoppers. However, even butyl rubber is not absolutely tight; air seeps in, and the storage time is correspondingly shortened. Loss of the subatmospheric pressure introduces additional problems in utilizing test tubes which contain a dosed quantity of reagent material, since an exact relation between the quantity of reagent material and the quantity of blood being sampled must be maintained, in the taking of the samples, and inaccuracies are introduced inasmuch as the quantity of blood drawn in under the subatmospheric pressure depends of course on what the subatmospheric pressure in the test tube is.

As a result, evacuated test tubes normally have to be packed in evacuated containers, so as to increase storage stability. This further increases the cost of manufacture and distribution. Nonetheless, despite the high cost of production, vacuum tubes are not quite satisfactory, since despite every precaution after the container is opened, since they are not absolutely leak tight, the subatmospheric pressure decreases with storage.

Accordingly, Svensson in U.S. Pat. No. 3,776,218 proposed a system in which the container receiving the sample is delivered as an open container, and the necessary subatmospheric pressure is drawn at or shortly before the sample is taken. This system has its drawbacks, however, since the test tubes must then be sterilized before they can be used; this problem is not presented in the case of vacuum tubes, which are not only evacuated but sterilized, and kept sterile until used because they are sealed.

Nehring U.S. Pat. No. 3,469,572, patented Sept. 30, 1969, provides a fluid sampling device having a housing which includes a double-ended cannula. One end of the cannula is adapted to be connected to a fluid source to be sampled, and the other end has a valve, which is normally closed but opens when fluid is to pass through the cannula from the fluid source to the fluid collection container which has previously been evacuated.

The objective of the Nehring device is to allow multiple sampling from a single puncture of a vein. The needle is allowed to remain in the vein, and the closed valve prevents loss of blood through the cannula while the blood collection container is changed. Blood collection containers that are evacuated are employed, so that the blood is sampled entirely automatically, with no additional equipment, without loss of blood, and without the need for resterilization processes.

In accordance with the instant invention, the disadvantages of pre-evacuated containers are overcome by using containers sealed against contamination at atmospheric pressure. The necessary reduction in pressure of the container prior to sampling is effected at or shortly before the sample is taken. One can therefore use less costly material for the containers, and can accurately adjust the subatmospheric pressure drawn according to the size of the sample being taken. One can also know what the subatmospheric pressure is in the container, at the time of sampling.

The method in accordance with the invention for the preparation of containers such as test tubes and the collection of medium samples therein comprises the preliminary step of sealing the container at substantially atmospheric pressure by a resilient stopper well prior to the collection of the sample; and then, at or shortly before the time of collection of the sample, piercing the stopper by a first cannula connected at one end to a pressure-reducing device, thereby connecting the interior of the container with the pressure-reducing device via the first cannula; evacuating the container to a desired subatmospheric pressure; withdrawing the first cannula; penetrating the stopper by a second cannula connected at one end to a medium source, thereby connecting the source with the interior of the container via the second cannula; and then sucking medium into the container under the influence of the subatmospheric pressure effected by means of the pressure reduction.

The apparatus in accordance with the invention comprises, in combination, holder means movable reciprocably and retaining a container sealed by a resilient stopper; means movable towards and away from the stopper, and including a first cannula for piercing the stopper and communicating with the interior of the container; means providing a fluid flow connection from the interior of the container via the pierced stopper and the first cannula with a pressure-reducing device, reducing the pressure in the container to a desired subatmospheric pressure; means including a second cannula for piercing the stopper and communicating with the interior of the container; means providing a fluid flow connection to the interior of the container via the pierced stopper and the second cannula with a supply of medium to be sampled for sucking such medium into the container under the subatmospheric pressure effected in the reduction in pressure in the container.

This apparatus is especially intended for use in the reduction in pressure and collection of medium samples in standardized containers such as test tubes, sealed and sterilized at substantially atmospheric pressure.

In a preferred embodiment of the apparatus of the invention, the pressure-reducing device comprises a piston and cylinder, the piston being reciprocatable within the cylinder by the container to define a chamber on one side of the piston that expands on the one stroke and contracts on the next stroke, the first cannula upon piercing the stopper putting the interior of the container into communication with the chamber on one side of the piston while it is expanding. The expansion of the chamber during that stroke of the piston reduces the pressure in the container; the container being reciprocatable with the holder means and the piston towards and away from the second cannula, moves toward the second cannula on the one stroke of the piston while the chamber is expanding, for piercing of the stopper thereby in a limiting position of the piston on the one stroke.

Preferred apparatus for the collection of medium samples in such containers, exemplified by a standard size test tube sealed at substantially atmospheric pressure, are shown in the drawings, in which:

FIG. 1 is a longitudinal section through a device for taking samples of blood, showing a test tube attached, with the stopper pierced by the first cannula, ready for reduction in pressure therein, prior to collection of a sample;

FIG. 2 is a longitudinal section of the device of FIG. 1, showing the test tube after pressure has been reduced for sample collection, in position for piercing the stopper by the second cannula, opening the connection to the medium source to be sampled;

FIG. 3 is a further longitudinal section of the device of FIG. 1, with the test tube collecting a sample after piercing the stopper by the second cannula;

FIGS. 5 to 8 show later stages in the operation sequence of the device of FIG. 4;

FIG. 5 is a longitudinal section through the device of FIG. 4, showing the position of the test tube in the device after piercing of the stopper by the first cannula, for pressure reduction;

FIG. 6 is a longitudinal section of the device of FIG. 4, showing the position of the test tube after withdrawal of the first cannula, and ready for piercing of the stopper by the second cannula;

FIG. 7 is a longitudinal section of the device of FIG. 4 showing the position of the test tube after piercing of the stopper by the second cannula, during collection of the sample via the second cannula;

FIG. 8 is a longitudinal section of the device shown in FIG. 4, showing the test tube ready to be withdrawn from the device, after collection of the sample;

FIG. 9 is a cross-sectional view of the device as shown in FIG. 8, taken along the line 9—9;

FIG. 10 is a perspective view showing an embodiment of the stopper which permits horizontal collection of a sample when the container contains a liquid reagent;

FIG. 11 is a longitudinal section through the stopper of FIG. 10; and

FIG. 12 is a cross-sectional view taken along the line 12—12 of FIG. 11;

FIG. 13 is a longitudinal section through a modified stopper and container arrangement; and FIG. 14 is a longitudinal section through a further modified stopper and container arrangement.

Figure 4:
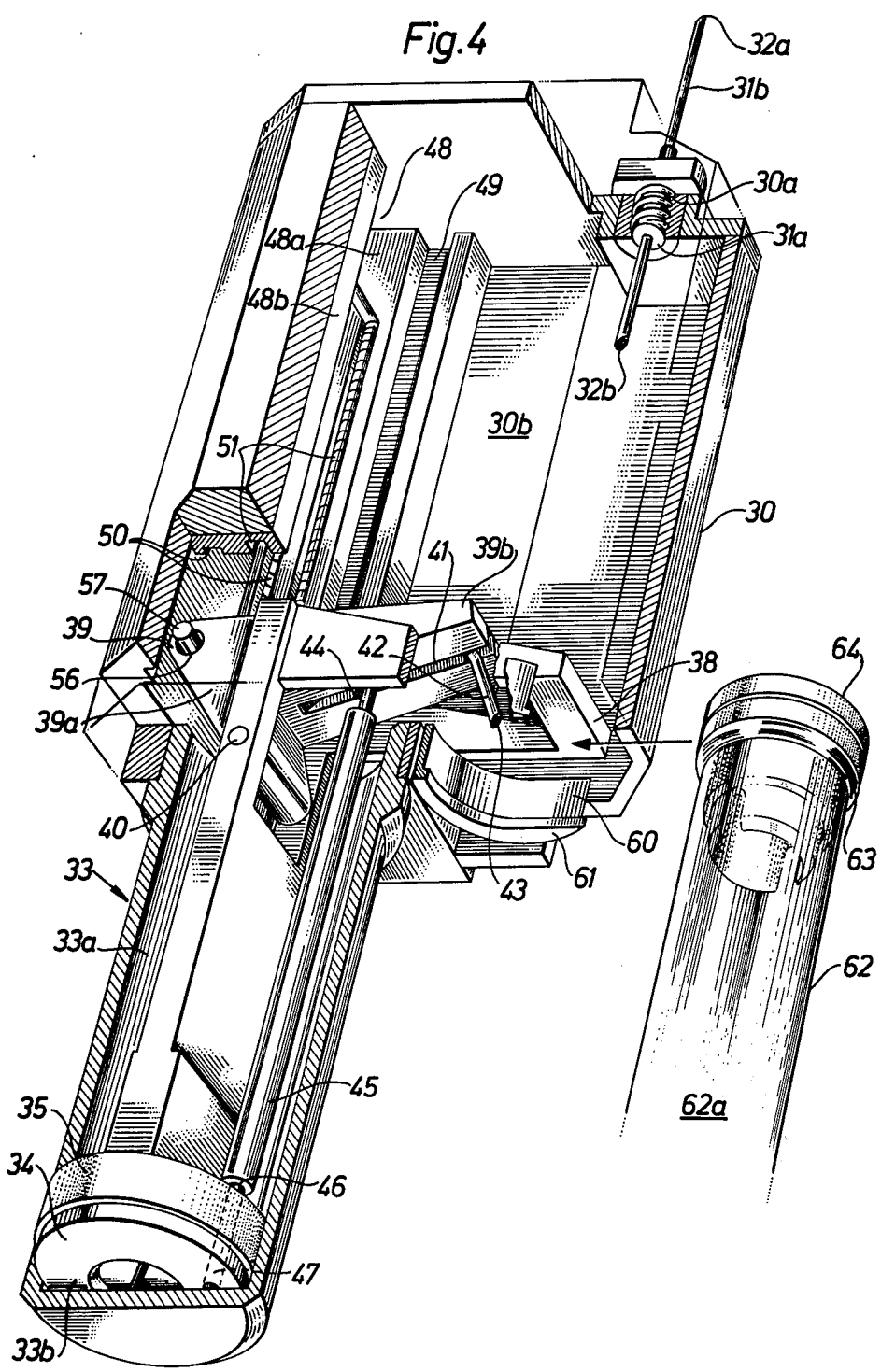
FIG. 4 shows in perspective another embodiment of apparatus in accordance with the invention, the structure being partly cut away to show in longitudinal section certain internal parts; a test tube is shown as an example of a container, ready to be inserted in the holder of the device, in the start of the preparation of the tube for collection of a sample.

The device shown in FIGS. 1 to 3 has a test tube holder 10 of injection-molded plastic having an internally threaded aperture 10a at the top into which is screwed an externally threaded stopper 10b carrying a cannula 11, with a pointed external tip 11a, for insertion into a blood vessel of a patient, and a pointed inner tip 12, for piercing the resilient stopper 14 of a test tube 13 in which a blood sample is to be collected. In this case, the test tube 13 is provided with a resilient stopper 14 of butyl rubber or equivalent material. Any resilient material can be used, however, it being desirable solely that the material be sufficiently resilient and sufficiently soft that the cannula can pierce it without undue difficulty, and preferably, that when the cannula is withdrawn, the stopper will be self-closing and -sealing, due to the natural resiliency of the material, so that the sample collected will not leak out, and be lost.

The test tube 13 is sealed with the stopper 14 under atmospheric pressure, and prior to sealing it is sterilized. The seal is sufficiently tight that sterility is maintained until use. If desired, the test tube may contain an accurately measured dose of liquid or solid reagent material desired to react with the blood sample that is collected and give an analytical indication of the condition being observed.

Since the test tube is sealed under atmospheric pressure, it has no tendency to acquire air by seepage from the surrounding atmosphere, as in the case of an evacuated test tube. Therefore, neither the tube nor the stopper need be of absolutely leak tight or diffusion tight material, such as glass, although glass can of course be used. Less costly material such as plastic, for instance, heat-resistant polyethylene, polypropylene, polystyrene or polyvinyl chloride, if desired, having an inside coating of silicone polymer, can also be used.

The holder 10 is intended to be used for collection of blood samples in standardized test tubes of the same type as conventional vacuum tubes. The difference resides in the fact that since the interior contents of the tube are at normal atmospheric pressure, the tube must be brought to a desired subatmospheric pressure before the sample is drawn. The mechanism provided for this purpose is as follows:

The holder 10 is cylindrical, and is provided with an aperture 10c at the opposite end to the cannula 11. Within the cylinder 10 is concentrically disposed a further cylinder 17, defining with outer cylinder 10 a first annular piston chamber 15, within which is reciprocated an annular piston 16. Within the cylinder 17 is defined a second piston chamber 17a, and within chamber 17a is disposed a reciprocable piston 18 directly in line with the aperture 10c, for a purpose presently to be seen. The piston 18 is keyed via slots (not visible in the drawing) to projections 19 in the wall of cylinder 17, so that the piston 18 cannot be rotated. The piston carries a cannula 20, which extends through and has a limited axial displacement in the piston. The cannula 20 is in flow connection via a flexible tube 21 with the space 15a in the first annular piston chamber 15, above the annular piston 16. The piston 18 is in operative connection via aperture 23 in the wall of cylinder 17 with the annular piston 16 by a number of flexible cords 22, so that when the piston 18 is moved towards cannula 11 within piston cylinder 17, the annular piston 16 is pulled in the opposite direction, in annular chamber 15. The aperture 23 through which the cords pass also serves to vent the space 15b of chamber 15 below the piston 16, as the piston is displaced in this direction.

In the piston 16 there is provided a check valve (not seen in the drawing) which is closed when the piston is moved into space 15b, but which allows the air to flow from one side of the piston to the other when the piston is moved into space 15a.

The piston 18 has a central aperture 24 receiving cannula tip 12. On the top of the piston 18, there is a wedge 25, which cooperates with a collar or similar on the cannula 20. At the upper end of the cylinder 17 there is provided a cam surface 27, which is engaged by the wedge 25 when the piston 18 is at this end of the cylinder 17, camming the wedge 25 sideways under the collar 26, so that the cannula 20 is moved away from piston 18. The cannula 20 can be spring-biased towards piston 18, and the wedge 25 can also be spring-biased in such a way that it will remain in the position shown in FIG. 3 until the piston 18 returns to its position in the other end of the cylinder 17, as shown in FIG. 1.

The tube 13 and stopper 14 are inserted in aperture 10c and the stopper is brought into engagement with the cannula 20, by pushing the tube against it. The cannula pierces the stopper 14, and so connects the interior of the test tube 13 with the space 15a above the piston 16, as shown in FIG. 1. To retain the piston 18 in position, to resist movement while the cannula 20 is being thrust against and pierces the stopper 14, a suitable pressure point can be provided for the piston at that end of the cylinder 17. When the stopper has been pierced, application of more force to the tube 13 forces piston 18 to move from the pressure point into cylinder 17. The piston 16 is simultaneously pulled in the opposite direction by cords 22. This enlarges space 15a, and the pressure in the interior of the test tube 13 is thereby decreased. In this way, by the time the tube has been brought into the position shown in FIG. 2, the tube is ready to draw in a sample.

The tube 21 can be guided in a suitable way, in order to be rolled up, or folded, or coiled, as the piston 18 is moved into the cylinder 17, so that the tube is held away from the cannula tip 12, and so that it does not interfere with the movement of the piston 18 and the wedge 25.

Continued pushing in of the tube 13 brings the stopper 14 into contact with the tip 12 of the cannula 11. The tip of the cannula first passes through the aperture 24, and then engages and pierces the stopper 14. Before the tip reaches into the interior of the test tube, the wedge 25 engages the cam surface 27, and is displaced to the right, as seen in FIG. 3, so that the point of the cannula 20 is lifted out of the interior of the test tube, to a position inside or above the stopper 14. The result is that, due to the resiliency of the stopper, the opening formerly made by the cannula 20 is closed before the cannula 11 has pierced the stopper. Thus, the cannula 20 is prevented from coming into contact with the blood that flows into the test tube via the cannula 11 and there is therefore no contamination of one sample with another.

Eventually, in the limiting position of the piston 18, the stopper 14 is fully pierced by the cannula 11, and blood is collected through the cannula in the test tube.

When the desired quantity of blood has flowed in, the test tube 13 is withdrawn. As it is withdrawn, the piston 18 is brought with it, and the cannula tip 12 is withdrawn, thereby closing the stopper 14. The passage through the cannula 11 is shut off by means of a valve located on the cannula tip 12.

So that the piston 18 may follow the test tube 13 as it is withdrawn, suitable means such as a bayonet joint can be provided for the connection of the outer face of the piston 18 and the stopper 14, when the test tube is inserted into aperture 10c, and for their disengagement when the test tube has been pulled down so far that the piston 18 is at its other limiting position at the outer end of the chamber 17a. The test tube with the stopper in it is then disengaged from the piston 18, while the cannula tip 11a is retained in the punctured blood vessel. Since the cannula 11 is closed by a valve, there is no drainage of blood from the patient, and another test tube can now be inserted and evacuated, for collection of another sample of blood.

The device shown in FIGS. 4 to 9 comprises a holder 30 which also can be made of injection-molded plastic. An internally threaded aperture 30a is provided in one wall, and in this aperture is screwed an externally threaded stopper 31a carrying a cannula 31b having a pointed outer tip 32a and a pointed inner tip 32b.

To another wall of the holder 30 is attached a piston and cylinder assembly 33, having an internal piston chamber 33a in which a piston 34 is reciprocatably movable. The piston 34 sealingly engages the walls of the piston chamber 33a via the seal ring 35.

The piston rod 36 attached to piston 34 reciprocates into the open interior 30b of the holder 30, and carries a laterally-extending frame 38, disposed entirely within the interior space 30b. An actuating lever 39 having two arm sections 39a and 39b extending at an angle to each other from its pivot point 40, is pivotably connected to the end of the piston rod 36 via shaft 40, for pivoting movement about an axis extending transversely to the piston rod.

One side of the arm 39a carries a groove 41, in which is fixed a U-shaped cannula 42, having a pointed tip 43 and a U-shaped arm 44 in fluid flow connection with a flexible tube 45.

The tube 45 runs through the piston chamber 33a, alongside but spaced from the piston rod 36, and is connected at its end to a stub tube 46 fixed on the inner face of the piston 34. The stub tube communicates with a bore 47 in the piston, which opens into the space 33b of piston chamber 33a on the outer side of the piston, thus making it possible to reduce the pressure in the interior of a test tube in fluid flow connection with the cannula 42, as the piston 34 is moved into the holder space 30b, as will presently be seen.

The holder 30 has a channel 48 on one side wall of the space 30b. The channel 48 has peripheral side walls 48a, 48b, carrying opposed grooves 49. The grooves 49 serve as tracks for the piston rod 36, engaging the sides of the rod 36, and preventing rotation of the piston.

In each of the opposed side walls 48a, 48b of the channel 48 there are parallel grooves 50 and 51. The groove 51 terminates in one end portion 52 proceeding at an angle towards and crossing groove 50 at 53, and a further end portion 54 extending from the other end of the groove 51 towards the groove 50 and crossing 50 at 55.

As is best seen in FIG. 9, the groove portion 51 is deeper than groove 50. However, the end portion 52 successively decreases in depth from groove 51 towards groove 50, so that the groove 50 is deeper than the end portion 52 at the crossing 53, as indicated in FIGS. 5 to 8. The end portion 54 has a depth that increases from groove 51 towards groove 50, so that the end portion 54 is deeper than groove 50 at crossing 55, as shown in FIGS. 5 to 8.

In the lever 39 there is a bore 56 at the angled central portion, where arms 39a and 39b meet, and this bore carries two cylindrical pins 57, spring-biased by compression coil spring 59 for axial displacement in the bore. The spring is retained by flanges 58, on the pins, and biases the two pins away from each other. The outer ends of pins 57 are slideably received in the groove system comprising grooves 50, 51, 52 and 54.

The frame 38 on the same side thereof as the piston and cylinder assembly 33 carries a U-shaped cylindrical socket 60 of a diameter corresponding to the largest diameter of the stopper 64 and end of a test tube 62, in which a sample is to be collected, and has a flange 61 reducing this diameter somewhat, to the outside diameter of the tube 62. The typical test tube shown as 62 has a flange 63 at its open end, which is closed off and sealed by the resilient stopper 64 of rubber or plastic material. The flange 63 is larger in diameter than the opening defined by the flange 61, but fits in the socket 60, so that the flange 61 retains the tube in position in the socket.

The sequence of steps in the operation of the device to collect a sample is shown in FIGS. 4 to 9.

The first step is to insert the test tube (as shown in FIG. 4) into the socket 60, in the manner seen in FIG. 5. For the start, the piston 34 should be at the bottom of the piston chamber 33a, in the position seen in FIG. 4, while the pins 57 of the lever 39 are in the groove end portion 54. The lever 39 is thus pivoted to the position shown in FIG. 4.

The test tube 62 in the socket 60 is now moved inwardly, and so comes into engagement with the frame 38. In consequence, the piston rod 36 and piston 34 are moved inwardly with the test tube, so that the space 33b on the outer side of the piston begins to enlarge. The pins 57 slide along the groove portion 54, and as they do so the lever 39 and arms 39a and 39b, guided by the movement of the pin 57 in the groove 54, are swung towards the stopper 64, into the position shown in FIG. 5. In this position, the tip 43 of the cannula 42 is pressed against and eventually pierces the stopper 64, opening the interior space 62a of the test tube into fluid communication with the tube 45, and since the tube is in communication with the space on the outer side of the piston 34, as this space enlarges the pressure in the interior of the test tube is reduced.

The tube is continued to be pushed inward. By the time the test tube has reached the position shown in FIG. 6, the pressure in the interior of the test tube has been reduced to the desired subatmospheric pressure. The pins 57 now enter the groove portion 52, and effect a return pivoting of the lever 39, withdrawing cannula 42 from the stopper 64, into the position shown in FIG. 6. As the cannula is withdrawn, the stopper 64 of course seals again, due to the resiliency of the stopper material. Since the interior of the holder 30 is open to the atmosphere, this automatically brings the space 33b beyond the piston 34 in the piston 33a into connection with the surrounding atmosphere, and it consequently comes at once to atmospheric pressure, while the reduced pressure created in the tube 62 is of course maintained, because the stopper has now sealed again. The test tube is now ready for connection to the sample collecting device.

With continued movement of the test tube towards the cannula tip 32b, the stopper 64 eventually comes into contact with the sharp tip 32b, of the cannula, which pierces the stopper, and brings it into fluid flow connection with the low pressure interior of the test tube. The tube is now in the position shown in FIG. 7. Assuming that the outer tip 32a has been brought in flow connection with a blood vessel of the patient, a blood sample can now be taken, being drawn into the test tube under the subatmospheric pressure in the tube, and is collected in the tube, as shown in FIG. 7.

When the test tube 62 has been brought to the limiting innermost position shown in FIG. 7, the pins 57 sliding along the groove portion 52 reach the crossing 53, where the pins 57 under the bias of the spring 59 snap into the deeper groove 50.

The test tube 62, now containing the blood sample, is then withdrawn from the holder 30. This operation is shown in FIG. 8. As this is being done, the frame 38 is carried with the test tube (due to the interengagement of the flange 61 and the flanged end 63 of the test tube 62). Thus, the piston rod 36 and the piston 34 are brought again towards the starting position shown in FIG. 4 in which they are at the outer end of the piston chamber 33a. While this is being done, the lever 39 is maintained in the position shown in FIG. 8, with the cannula 42 withdrawn from the stopper 64, because the pins 57 slide along the groove 50, and this causes no pivoting of the lever.

When the test tube 62 reaches the lower end of the holder 30, the pins 57 snap into the groove portion 54 at the crossing 55 under the bias of spring 59, because the groove portion 54 is deeper than groove 50 at the crossing. When the test tube has been detached from the frame 38 and removed, the device is now ready for preparing the next test tube for a blood sample, and the entire operation can be repeated.

The device is easily used for taking a number of blood samples, in sequence, without changing the blood connection to the patient, if a valve be provided on the cannula 31.

In many cases, test tubes used for taking blood samples are prefilled with an accurately measured amount of reagent. The device according to the invention can be held in a substantially horizontal position in the course of the operations shown in FIGS. 4 to 8 without risk that the reagent will be withdrawn through the cannula 42 when the pressure in the interior of the tube is being reduced, in the operation shown in FIG. 5, if the stopper used in the test tube is of the type shown in FIGS. 10 to 12. This arrangement also makes it impossible to use test tubes which have a different kind of stopper, thus preventing accidental use of another kind of test tube, with resultant spillage or loss of the reagent in the test tube, during evacuation.

The stopper 84 shown in FIGS. 10 and 11 has an end surface formed with an annular groove 71 surrounding a central recess 72. The portion 73 forms a tight seal in the open end of a test tube 62, so as to make the test tube airtight when the stopper is inserted therein. The outermost portion of the stopper has an enlarged portion 74, which extends out from the test tube, with the sealing portion 73 closing off the mouth of the test tube, and at the inner end there is a narrower portion 75 joining with the sealing portion 73 at a frustoconical transition 76.

The inner end of the stopper has a central passage 77 and an annular passage 78. The annular passage is closed off by a filter 79, which is not wetted by the liquid contents of the test tube, whether in the form of reagent or blood sample, but is permeable to gas.

The frame 38 is provided with an annular flange 80 spaced from the socket 60, and this flange is so located and dimensioned as to fit into the annular groove 71 on the end face of the stopper. In this case, the socket 60 does not require a flange 61, as in the embodiment of FIGS. 4 to 9, and therefore none is provided. The flange is replaced by a bayonet-type joint, a projection 81, which locks onto the end of flange 63 of a test tube 62, in a manner that will now be seen.

When the test tube 62 shown in FIGS. 10 to 12 is to be attached to the holder 30 on frame 38, the upper end closed by the stopper 84 is pushed from below in a slightly inclined position, as indicated by the arrow in FIG. 11, in order to push the flange 80 into the annular groove 71 in the stopper. Due to the flexibility of the resilient stopper, this is possible, because the stopper gives way during the insertion. Then, the test tube 60 is turned to the right or to the left, to a position in which it extends substantially parallel to the cylinder 33, so that the flanged end 63 of the test tube engages with the projection 81. This engagement is sufficient to obtain an operative connection between the test tube and the frame 38, so that the frame and the piston and other components connected therewith are moved by withdrawal of the test tube from the holder after a sample has been collected, inasmuch as the movement of the piston 34 does not involve any considerable resistance.

The annular passage 78 is so positioned in relation to the cannula 42 that the sharp tip 43 of the cannula pierces the stopper at the base 78a of the annular passage 78. This passage is always kept liquid-free, because the filter 79 is not wettable by liquid, but it is permeable to gas, thus permitting evacuation of the tube but not escape of any liquid in the tube. On the other hand, the inner tip 32b of the second cannula pierces the stopper at the base 77a of the central passage 77. Thus, the blood being collected enters the tube via the passage 77, and since this passage is not provided with a filter, the sample can be collected, and moves freely through the stopper into the interior of the test tube.

The modified stopper 85 is shown in FIG. 13 has an end surface formed with an annular groove 71 surrounding a central recess 72. The outermost portion of the stopper has an enlarged portion 74 which extends out from the test tube and is extended downwardly to form a collar 86 spaced from portion 75 which in this case joins portion 74. Thus there is provided between portion 74 and collar 86 an annular groove 87 opening downwards which receives an upper extension 88 of the test tube 62 projecting from flange 63. In this case the stopper seals the test tube at the outer surface of extension 88.

In the modified stopper 89 shown in FIG. 14 the test tube is sealed by the same arrangement as in FIG. 13 but there is no portion 75 provided on the stopper. In the embodiment of FIG. 14 the stopper 89 can be manufactured at a mimimum expense of material.

The device in accordance with the invention is primarily intended for use in the collection of samples of blood, but it can also be used for the collection of specimens of any kind of body fluid or medium, such as urine, and secretions of any kind.

It is not necessary of course that the pressure within the test tube be reduced immediately before the taking of a sample. The pressure can be reduced and the tube then allowed to stand until the sample needs to be taken, since the device is airtight, and therefore there will be no appreciable loss of the subatmospheric pressure created in the test tube in the course of the pressure reduction.

Having regard to the foregoing disclosure, the following is claimed as inventive and patentable embodiments thereof:

1. Apparatus for the evacuation of containers sealed at substantially atmospheric pressure by a resilient stopper well prior to the collection of the sample, and the collection of medium samples therein, which comprises, in combination, holder means movable reciprocably and retaining a container sealed by a resilient stopper, means movable towards and away from the stopper, and including a first cannula for piercing the stopper and communicating with the interior of the container, means providing a fluid flow connection from the interior of the container via the pierced stopper and the first cannula with a pressure-reducing device, reducing the pressure in the container to a desired subatmospheric pressure; the means movable towards and away from the stopper being capable of withdrawing the first cannula from the interior of the container sufficiently to permit the stopper to close after such withdrawal; means including a second cannula for penetrating the stopper after such withdrawal and communicating with the interior of the container; and means providing a fluid flow connection to the interior of the container via the pierced stopper and the second cannula with a supply of medium to be sampled for sucking such medium into the container under the subatmospheric pressure effected in the reduction in pressure in the container.

2. Apparatus according to claim 1, in which the holder means is adapted to receive a test tube as the container, sealed and sterilized at substantially atmospheric pressure.

3. Apparatus according to claim 1, in which the pressure-reducing device comprises a piston and cylinder, the piston being reciprocatable within the cylinder by the container to define a chamber on one side of the piston that expands on the one stroke and contracts on the next stroke, the first cannula upon piercing the stopper putting the interior of the container into communication with the chamber on one side of the piston while it is expanding, the expansion of the chamber during that stroke of the piston reducing the pressure in the container.

4. Apparatus according to claim 3, in which the container is reciprocable with the holder means and the piston towards and away from the second cannula, moving toward the second cannula on the one stroke of the piston while the chamber is expanding, for piercing of the stopper thereby in a limiting position of the piston on the one stroke.

5. Apparatus according to claim 3, in which the first cannula is operatively connected to and moved by the piston into and away from piercing engagement with the resilient stopper on the container.

6. Apparatus according to claim 5 in which the first cannula is pivotably mounted on the piston and is pivoted into and out from piercing engagement by a cam riding in a track on a wall of the cylinder.

* * * * *